United States Patent
Liu et al.

(10) Patent No.: US 11,998,299 B2
(45) Date of Patent: Jun. 4, 2024

(54) SCAN-LESS OPTICALLY COMPUTED OPTICAL COHERENCE TOMOGRAPHY USING A SPATIAL LIGHT MODULATOR

(71) Applicant: New Jersey Institute of Technology, Newark, NJ (US)

(72) Inventors: Xuan Liu, Berkeley Heights, NJ (US); Yahui Wang, Harrison, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 165 days.

(21) Appl. No.: 17/185,182

(22) Filed: Feb. 25, 2021

(65) Prior Publication Data
US 2021/0267457 A1 Sep. 2, 2021

Related U.S. Application Data

(60) Provisional application No. 62/983,098, filed on Feb. 28, 2020.

(51) Int. Cl.
*A61B 5/00* (2006.01)
*A61B 5/026* (2006.01)

(52) U.S. Cl.
CPC .......... *A61B 5/0066* (2013.01); *A61B 5/7257* (2013.01); *A61B 5/0261* (2013.01); *A61B 2562/0233* (2013.01); *A61B 2576/00* (2013.01)

(58) Field of Classification Search
CPC ... A61B 5/0066; A61B 5/7257; A61B 5/0261; A61B 5/0042; A61B 2562/0233;
(Continued)

(56) References Cited

U.S. PATENT DOCUMENTS

2004/0233944 A1* 11/2004 Dantus ............... G01B 9/02014
372/25
2006/0100528 A1* 5/2006 Chan ..................... A61B 3/102
600/476

(Continued)

OTHER PUBLICATIONS

Zhang, X., Huo, T., Wang, C et al. Optical computing for optical coherence tomography. Sci Rep 6, 37286 (2016). https://doi.org/10.1038/srep37286 (Year: 2016).*
(Continued)

*Primary Examiner* — Serkan Akar
*Assistant Examiner* — Neshat Baset
(74) *Attorney, Agent, or Firm* — Lerner David LLP

(57) ABSTRACT

An optically computed optical coherence tomography (OC-OCT) technology is disclosed. The OC-OCT system performs depth resolved imaging by computing the Fourier transform of the interferometric spectra optically. The OC-OCT system modulates the interferometric spectra with Fourier basis function projected to a spatial light modulator and detects the modulated signal without spectral discrimination. The optical computation strategy enables volumetric OCT imaging without performing mechanical scanning and without the need for Fourier transform in a computer. OC-OCT performs Fourier transform signal processing optically, without the need of mechanical scanning, and before data acquisition unlike traditional OCT methods and systems. The scan-less OCT imaging is achieved through the use of spatial light modulator (SLM) that precisely manipulates light wave to generate output with desired amplitude and phase.

8 Claims, 4 Drawing Sheets
(4 of 4 Drawing Sheet(s) Filed in Color)

(58) Field of Classification Search
CPC .......... A61B 2576/00; A61B 2576/026; G01B 9/02044; G01B 9/02083; G01B 9/02091; G06E 3/003; G16H 50/20; G16H 30/40
See application file for complete search history.

(56) References Cited

U.S. PATENT DOCUMENTS

| | | | | |
|---|---|---|---|---|
| 2014/0320816 | A1* | 10/2014 | Abramoff | A61B 3/1225 356/326 |
| 2015/0002853 | A1* | 1/2015 | Hsu | G01B 9/02043 356/497 |
| 2015/0230708 | A1* | 8/2015 | Wang | A61B 5/0066 600/479 |
| 2016/0287154 | A1* | 10/2016 | Chong | A61B 5/0066 |
| 2020/0375452 | A1* | 12/2020 | Yao | A61B 3/102 |
| 2021/0207942 | A1* | 7/2021 | Winkelmann, Jr. | G01B 9/02091 |

OTHER PUBLICATIONS

Akkin, T. et al., "Detection of Neural Action Potentials Using Optical Coherence Tomography: Intensity and Phase Measurements with and without Dyes" Frontiers in Neuroenergetics, Aug. 2010, pp. 1-10, vol. 2.

Choma, M.A. et al., "Sensitivity Advantage of Swept Source and Fourier Domain Optical Coherence Tomography" Optics Express, Department of Biomedical Engineering, Duke University, Sep. 2003, pp. 2183-2189, vol. 11, No. 18, Optical Society of America.

Huang, D. et al., "Optical Coherence Tomography" HHS Public Access, Available in PMC Nov. 2015, pp. 1-12, vol. 254 (5035).

Jia, Y. et al., "Quantitative Optical Coherence Tomography Angiography of Choroidal Neovascularization in Age-related Macular Degeneration" NIH Public Access, Available in PMC Jul. 2015, pp. 1-22, vol. 121 (7), American Academy of Ophthalmology.

Leitgeb, R. et al., "Performance of Fourier Domain vs. Time Domain Optical Coherence Tomography" Department of Medical Physics, University of Vienna, Apr. 2003, pp. 889-894, vol. 11, No. 8, Optical Society of America.

Liu, X. et al., "Towards Automatic Calibration of Fourier-Domain OCT for Robot-Assisted Vitreoretinal Surgery" Optics Express, Nov. 2010, pp. 24331-24343, vol. 18, No. 23, Optical Society of America.

Maurer, C. et al., "What Spatial Light Modulators can do for Optical Microscopy" Laser Photonics Reviews 5, No. 1, Dec. 2010, pp. 81-101, WILEY-VCH, Weinheim.

Qiu, Y. et al., "Quantitative Optical Coherence Elastography based on Fiber-optic Probe for in situ Measurement of Tissue Mechanical Properties" Biomedical Optics Express, Jan. 2016, pp. 688-700, vol. 7, No. 2, Optical Society of America.

Solli, D.R. et al., "Analog Optical Computing" Nature Photonics, Nov. 2015, pp. 704-706, vol. 9, Macmillan Publishers.

Wojtkowski, M. et.al., "Three-dimensional Retinal Imaging with High-Speed Ultrahigh Resolution Optical Coherence Tomography" NIH Public Access, Available IN PMC Aug. 2007, pp. 1-23, vol. 112(10).

Zhang, W. et al., "Optical Computing Optical Coherence Tomography with Conjugate Suppression by Dispersion" Optics Letters, Apr. 2019, pp. 2077-2080, vol. 44, No. 8, Optical Society of America.

Zhang, Z. et al., "Single-pixel Imaging by Means of Fourier Spectrum Acquisition" Nature Communications 6, Feb. 2015, pp. 1-6, Macmillan Publishers.

* cited by examiner

SCAN-LESS OPTICALLY COMPUTED OPTICAL COHERENCE TOMOGRAPHY USING A SPATIAL LIGHT MODULATOR

CROSS REFERENCE TO RELATED APPLICATION

This application claims priority from U.S. provisional application No. 62/983,098 filed Feb. 28, 2020, the disclosure of which is hereby incorporated herein by reference.

STATEMENT REGARDING FEDERALLY SPONSORED RESEARCH

This invention was made with government support under Agreement No. 1R15CA213092-01A1 awarded by the NIH. The government has certain rights in the invention.

FIELD OF DISCLOSURE

The present disclosure relates to three-dimensional (3-D) imaging technology. In particular, the present disclosure relates to an optically computed optical coherence tomography(OC-OCT) for volumetric imaging.

BACKGROUND

Traditionally, optical coherence tomography (OCT) is a high-resolution cross-sectional imaging modality that has found applications in a wide range of biomedical fields, such as ophthalmology diagnosis, interventional cardiology, surgical guidance, and oncology. OCT can be used to image dynamic scenes, in quantitative blood flow sensing and visualization, dynamic optical coherence elastography, and large-scale neural recording.

However, the spatiotemporal resolution of OCT for dynamic imaging is limited by the approach it takes to scan the three-dimensional (3-D) space. In a typical OCT system, the incident light is focused to a point at the sample. The OCT system uses mechanical scanners (galvanometers or MEMS scanners) to steer the probing beam to scan the transverse plane and acquires an "A-scan" at each transverse coordinate. For volumetric imaging, the OCT system scans individual voxels in a 3D Cartesian coordinate sequentially, resulting a limited imaging speed. In addition to limited spatiotemporal resolution, the use of mechanical scanners results in bulky sample arm and complex system configuration.

Despite these disadvantages, optical coherence tomography (OCT) is a versatile, high-resolution tomographic imaging modality. Again, OCT has found a wide range of biomedical applications, such as ophthalmology diagnosis, surgical guidance, and tissue characterization for cancer research [1]. One emerging application of OCT is high-speed imaging of dynamic scenes, such as quantitative blood flow imaging, dynamic optical coherence elastography, and large scale neural recording [2-4]. In many applications of OCT, high-speed OCT imaging in a specific dimension such as in en face plane is more desirable than slow acquisition of the entire 3D volume. However, OCT imaging in an arbitrary dimension still has limited imaging speed, although on average it takes an extremely short period of time to acquire an OCT pixel [5].

To obtain depth resolved signal, time domain (TD) implementation of OCT performs mechanical scanning in axial (z) dimension and acquires pixels of an Ascan one after another sequentially. Fourier domain OCT (FD OCT) that was developed afterwards reconstructs all the pixels within an Ascan simultaneously, by taking Fourier domain measurement and calculating the Fourier transform of the interferometric spectrum in a computer. FD OCT eliminates mechanical scanning in the axial direction and offers significant advantage in imaging speed and sensitivity compared to TD OCT [6, 7]. Nevertheless, the strategy for 3D data acquisition remains the same for TD and FD implementations of OCT, and has become a major challenge in high-speed imaging of dynamic events.

For volumetric imaging in a Cartesian coordinate system (x, y, z), a conventional OCT system (both TD and FD techniques) performs fast axial (z) scanning, and performs slow scanning in x and y directions to generate a "Bscan" with multiple Ascans, as shown in FIG. 1 (a), and generate a Cscan using multiple Bscans, as illustrated in FIG. 1 (b), by steering the probing beam mechanically. The raster scanning strategy illustrated in FIGS. 1 (a) and 1 (b) allows high-speed B-mode OCT imaging, but results in an extremely slow speed for 2D imaging in any non-Bscan plane. Consider the plane shaded in green in FIG. 1 (b). The normal of the plane, n, is not along y axis of the Cartesian coordinate system. To obtain a 2D image from this plane, the OCT system has to scan the entire 3D volume and select pixels within the plane through post processing.

In addition to limiting the imaging speed, current strategy for 3D OCT data acquisition uses mechanical scanners (galvanometers, MEMS scanners, scanning motors, etc.) to steer the light beams, resulting in a bulky instrument footprint and complex system configuration. Moreover, the scanning of the 3D volume generates a huge amount of data. It is extremely challenging to acquire, transfer, process, and store the 3D image data. Optical computing that directly uses photons to carry out computation tasks may provide a more efficient way to address 3D spatial coordinate and manage massive data [8]. For example, in Ref [9] X. Zhang et al used arbitrary waveform generation to impose fast temporal modulation for optical computation in OCT imaging. However, conventional raster scanning approach for OCT data acquisition is cumbersome and does not address OCT voxels in 3D space.

Thus there still remains a need in the art for volumetric OCT imaging without mechanical scanning and without the need for Fourier transform in a computer.

BRIEF SUMMARY OF THE INVENTION

Compared to the current state of the art, the present disclosure fulfills the above criteria and provides additional benefits that state of the art systems cannot provide. Conventional optical coherence tomography system performs mechanical scanning to acquire image from 3D space and uses a computer to perform massive computation tasks for image reconstruction and data analysis. Optically computed optical coherence tomography (OC-OCT) eliminates the need for mechanical scanning in tomographic imaging and performs computation optically without the need to transfer the data into a computer.

In accordance with embodiments of the present disclosure, an optically computed OCT (OC-OCT) system and process are disclosed that takes an optical computation approach to perform Fourier transform and eliminates the need for mechanical scanning in 3D OCT imaging. Unlike conventional OCT where data acquisition is performed before signal processing, the OC-OCT system performs signal processing optically before data acquisition.

In one embodiment, the OC-OCT system includes a spatial light modulator (SLM). SLM has been used for optical pulse shaping, structured illumination, optical computation, and other applications of optical imaging [10, 11]. In the present embodiment, the present inventors exploit the capability of SLM in precisely manipulating a light wave to generate output with a desired amplitude and phase.

The use of spatial light modulator (SLM) that precisely manipulates light wave to generate output with desired amplitude and phase produces a scan-less OCT imaging technology that allows the observation of transient phenomena (neural activities, blood flow dynamics, and the like) with unprecedented spatiotemporal resolution.

In one embodiment, optical computation of Fourier transform is achieved by modulating the interferometric spectra with a programmable SLM and then performing spectrally non-discriminative detection. An optical computation strategy implemented for OCT imaging in the present disclosure is disclosed. In another embodiment, a method for volumetric OCT imaging through optical computation is disclosed.

Depending on the embodiment, the OC-OCT method and system further includes a highly innovative optical computation strategy to extract signal from a specific depth directly without signal processing in a computer. The optical computation module in OC-OCT performs Fourier transform optically before data acquisition, by calculating the inner product between a Fourier basis function projected by the spatial light modulator and the Fourier domain interferometric signal. OC-OCT allows phase resolved volumetric OCT imaging without mechanical scanning, and has the capability to image an arbitrary 2D plane in a snapshot manner.

Any combination and/or permutation of the embodiments is envisioned. Other objects and features will become apparent from the following detailed description considered in conjunction with the accompanying drawings. It is to be understood, however, that the drawings are designed as an illustration only and not as a definition of the limits of the present disclosure.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

To assist those of skill in the art in making and using the disclosed optically computed optical coherence tomography and associated systems and methods, reference is made to the accompanying figures, wherein.

DETAILED DESCRIPTION

Exemplary embodiments are directed to an Optically Computed-Optical Coherence Tomography (OC-OCT) system and process of using same. It should be understood that different embodiments could generally be applied. Optically computed OCT (OC-OCT) technology disclosed herein eliminates the need for mechanical scanning in 3D OCT imaging by employing a highly novel optical computation system to perform Fourier transform. For conventional Fourier domain OCT, data is acquired and transferred to PC where Fourier transform is performed to reconstruct depth profiles of the sample. OC-OCT performs signal processing optically before the signal is detected by the camera.

The optical computation procedure is achieved by using a spatial light modulator (SLM). SLM is known as being used in other applications such as optical pulse shaping, structured illumination, and optical computation. However, SLM has not been used in OCT imaging until now. Using SLM, light wave can be precisely modulated to have the anticipated amplitude and phase. The spectral interferogram output from a spectral domain OCT system is modulated by a programmable SLM to achieve Fourier transform optically. The signal is later detected without spectral discrimination. An optically computed two-dimensional image at a specific depth determined by the SLM pattern is thus produced. The optical computation strategy allows volumetric OCT imaging without axial or lateral mechanical scanning that is novel and has not been demonstrated before in this field.

Figure 3:
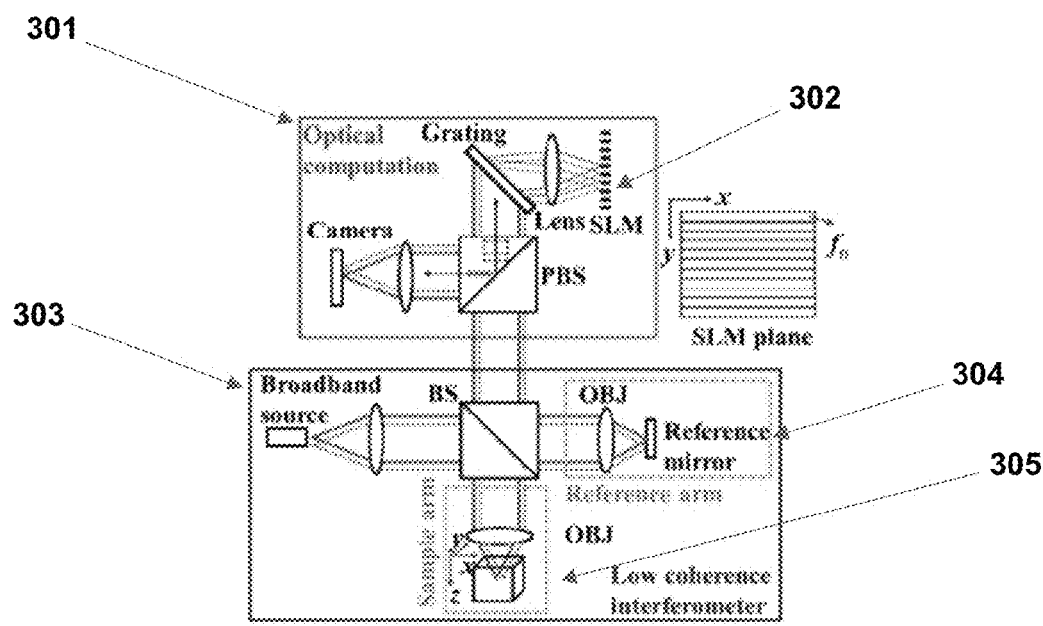
FIG. 3 shows one embodiment of an OC-OCT system.

Adverting to the figures, FIG. 3 shows one embodiment of an OC-OCT system that could include an optical computation module 301 having a spatial light modulator (SLM) 302, a polarization beam splitter (PBS). The OC-OCT system may also include a low coherence interferometer 303 having a beam splitter (BS), and a broadband source to illuminate the interferometer. The low coherence interferometer may also further include a reference mirror 304 and a sample arm 305 for the object (OBJ) being scanned. In the present embodiment, the SLM is sized to precisely manipulate a light wave to generate output with a desired amplitude and phase. In one embodiment, optical computation of Fourier transform is achieved by modulating the interferometric spectra with a programmable SLM and then performing spectrally non-discriminative detection.

OC-OCT is a Fourier domain technique that achieves depth resolution by optically Fourier transforming spectral interferogram. Consider an Ascan S ($S \in \mathbb{C}^N$ and $S=[s_1, s_2, s_3, \ldots, s_N]^T$). With sample light originating from a specific transverse coordinate, the interferometer generates a spectral interferogram M after a disperser. M is a 1D vector ($M \in \mathbb{R}^N$ and $M=[m_1, m_2, m_3, \ldots, m_N]T$) and is mathematically related to the spatial domain Ascan through Fourier transform: $S=FM$ which is more explicitly shown in Eq (1) ($s_n$ represents spatial domain OCT signal at the $n^{th}$ discrete depth in an Ascan; $m_k$ represents spectral signal at the $k^{th}$ wavenumber; $F \in \mathbb{C}^{N \times N}$ is the Fourier transform matrix and $Fnk=e^{j2\pi nk/N}$).

$$\begin{bmatrix} s_1 \\ s_2 \\ \ldots \\ s_N \end{bmatrix} = \begin{bmatrix} F_{11} & F_{12} & \ldots & F_{1N} \\ F_{21} & F_{22} & \ldots & F_{2N} \\ \ldots & \ldots & \ldots & \ldots \\ F_{N1} & F_{N2} & \ldots & F_{NN} \end{bmatrix} \begin{bmatrix} m_1 \\ m_2 \\ \ldots \\ m_N \end{bmatrix} \quad (1)$$

Figures 2A, 2B, 2C:
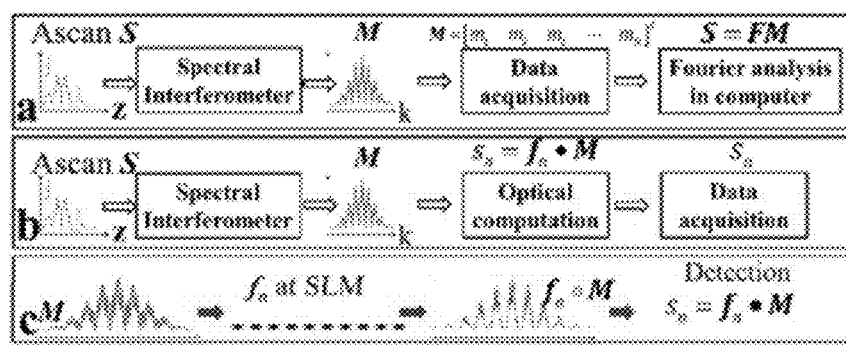
FIGS. 2A-2C show (a) data flow in a conventional FD OCT system; (b) shows data flow in an OCT system, in accordance with one embodiment of the present disclosure; (c) shows data flow in Fourier transform of spectral interferogram.

As illustrated in FIG. 2A, a conventional FD OCT system measures the entire interferometric spectrum M that has N discrete Fourier bins, streams the data into a computer, performs Fourier transform in the computer and reconstructs the entire Ascan. FIG. 2A also implies N Fourier bins have to be acquired to fully reconstruct the Ascan S, even if a small subset of pixels are of interest in the Ascan. OC-OCT takes a completely different approach to resolve a pixel in 3D space. One embodiment of the method performed by the OC-OCT system is shown in FIG. 2B.

According to the above Equation (1), $s_n$, the OCT signal at the $n^{th}$ discrete depth in an Ascan, can be expressed in Eq (2) that shows $s_n$ is the inner product between vector $f_n$ (the transpose of $n^{th}$ row of the Fourier matrix F) and vector M. In Eq (2), · indicates vector inner product.

$$s_n = F_{n1}m_1 + F_{n2}m_2 + \ldots + F_{nN}m_N \quad (2)$$

$$= [F_{n1} \; F_{n2} \; \ldots \; F_{nN}] \begin{bmatrix} m_1 \\ m_2 \\ \ldots \\ m_N \end{bmatrix}$$

$$= f_n \cdot M$$

Equation (2) provides an alternative approach to address a spatial location in OCT imaging. As illustrated in FIG. 2 (b), the OC-OCT system in this embodiment calculates $f_n \cdot M$ optically and directly obtains $s_n$ at the point of data acquisition. Optical computation of Eq (2) is further illustrated in FIG. 2 (c). The chosen Fourier basis function ($f_n$) is projected to the SLM along the dimension of spectral dispersion. The spectrum modulated by the SLM is essentially the element-wise product of $f_n$ and M ($f_n \cdot M$). The detector then performs spectrally non-discriminative detection, generating $s_n$, the inner product between vector $f_n$ and vector M.

The configuration of one embodiment of an OC-OCT system that allows depth resolved imaging with an extended field of view is illustrated in FIG. 3. The OC-OCT system could include a broadband source to illuminate the Michaelson interferometer with an extended field of view. A 2D reflective SLM is used for light modulation and a 2D camera is used for signal detection in this embodiment.

The imaging principle of the OC-OCT system is explained as follows. First, the OC-OCT configuration in FIG. 3 establishes a one-to-one mapping between the transverse spatial coordinate at the sample plane and at the detector plane, illustrated as solid and dashed light beam profiles in FIG. 3. This is similar to conventional light microscopy. Optical signal originating from transverse coordinate ($x_0, y_0$) at the sample is mapped to the same y coordinate ($y=y_0$) at the detector, because the light beam is not altered along y dimension by the grating or the SLM. On the other hand, the spectrum originating from different x coordinate arrives at the SLM plane with a global shift proportional to the x coordinate after the diffraction grating.

Figures 1A, 1B:
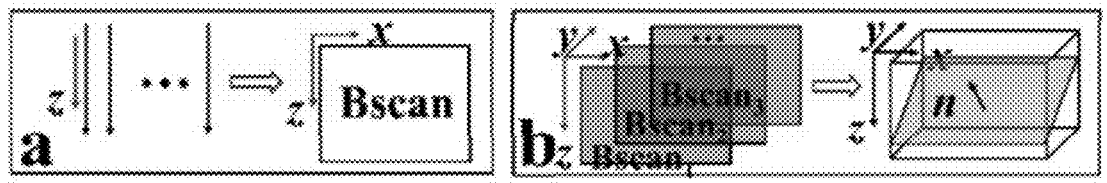
FIGS. 1A-1B show (a) a schematic of a conventional OCT system generating a Bscan using multiple Ascans; (b) is a schematic of a conventional OCT system generating a Cscan using multiple Bscans.

Reflected by the SLM and diffracted again by the grating, the light rays originating from ($x_0, y_0$) at the sample are collimated and eventually focused to ($x_0, y_0$) at the detector plane for spectrally non-discriminative detection, for a magnification of 1 from the sample plane to detector plane without loss of generality. On the other hand, depth resolution is achieved through optical computation. The diffraction grating disperses the output of the interferometer along x direction and the SLM projects a Fourier basis function ($f_n$) to its row at a specific y coordinate ($y=y_0$), as illustrated in the upper right inset of FIG. 3. Spectral interferogram originating from different x coordinate at the sample is modulated by a laterally (in x dimension) shifted version of $f_n$, which does not affect the results of optical computation of OCT signal magnitude. Spectrally non-discriminative detection of the modulated interferometric spectrum generates depth resolved OCT signal from the $n^{th}$ discrete depth, for pixels corresponding to different x coordinates. Notability, when all the rows of the SLM projects the same pattern for spectral modulation, the OC-OCT system generates an en face imaging from a specific depth. If different rows of the SLM project different Fourier basis functions, signals can be simultaneously obtained from different depths. Therefore, OC-OCT allows snap-shot imaging from an oblique plane (the green plane in FIG. 1B).

In one embodiment, the OC-OCT system shown in FIG. 3 could include a mounted LED (Thorlabs) at 470 nm with 25 nm bandwidth as the broadband source. The interferometric spectrum was dispersed by a 600/mm grating, modulated by a 2D SLM (Holoeye LC-R 720), and detected by a CMOS camera (Basler acA2000). The achromatic doublet lens in front of the SLM had a focal length of 250 mm and the achromatic doublet lens in front of the CMOS camera had a focal length of 100 mm. Identical objectives (20× Olympus, dry) were used in reference and sample arms of the interferometer.

To demonstrate 3D OC-OCT imaging within a large depth range, achromatic doublet was used as imaging objectives to obtain results shown in FIG. 7. Notably, a polarized beam splitter (PBS) was inserted between the Michaelson interferometer and the optical computation module to ensure unambiguous amplitude modulation by the SLM and direct optical signal for detection. In FIGS. 6A-6D demonstrated is OC-OCT images of onion skin cells at different depths (a), (b), and (c); (d) image generated by averaging signal at different depths, wherein the scale bars represent 50 μm.

Prior to imaging experiments, the present inventors calibrated K(k) the mapping between the pixel index (k) in a row of SLM and the corresponding wavenumber K, because the pixels in a row of the SLM generally do not sample wavenumber domain spectral data uniformly. The calibration was achieved by measuring the interferometric spectrum obtained from a specular sample and enforcing linear phase [12]. The present inventors also calibrated R(v), the mapping between the value v projected to SLM pixels and the actual light reflectivity (R) of the SLM, because R(v) depends on the wavelength and polarization of the incident light, and is generally nonlinear. When v takes value of Fourier basis function ($F_{nk}$ in Eq (1)) and is directly projected to the $k^{th}$ pixel in a row of SLM pixels, the spectral modulation is non-sinusoidal, leading to diminished signal amplitude and ghost high harmonic peaks after optical Fourier transformation. To ensure that precise sinusoidal modulation was imposed to the interferometric spectrum, the present inventors projected the value of $R^{-1}(F_{nK(k)})$ to the $k^{th}$ pixel in a row of SLM pixels. Moreover, the SLM cannot directly generate complex exponential function needed in Fourier transform (Eqs (1) and (2)). Therefore, the present inventors projected cosine and sine patterns ($F_{cos}=(\cos(2\pi nK(k)/N)+1)/2$ and $F_{sin}=(\sin(2\pi nK(k)/N)+1)/2$) to the SLM. The present inventors temporally interlace $f_{cos}$ ($F_{cos}$ with k=1, 2, 3, . . . ) and $f_{sin}$ ($F_{sin}$ with k=1, 2, 3, . . . ) for spectral modulation, synchronized the data acquisition with the alternation of cos and sin patterns, acquired signals from cosine and sine channels ($s_{cos}=f_{cos}^T M - s_{DC}$ and $s_{sin}=f_{sin}^T M - s_{DC}$) and extracted the magnitude of the OC-OCT signal: $I=(s_{cos}^2+s_{sin}^2)^{1/2}$. With reference light much stronger than sample light, $s_{DC}$ could be estimated by $\Sigma m_k$ obtained with sample arm blocked. To simplify subsequent description, the present inventors refer the function projected to the SLM as $f_n$ that was generated after wavenumber calibration, reflectivity calibration, and temporal interlacing.

Figures 4A, 4B:
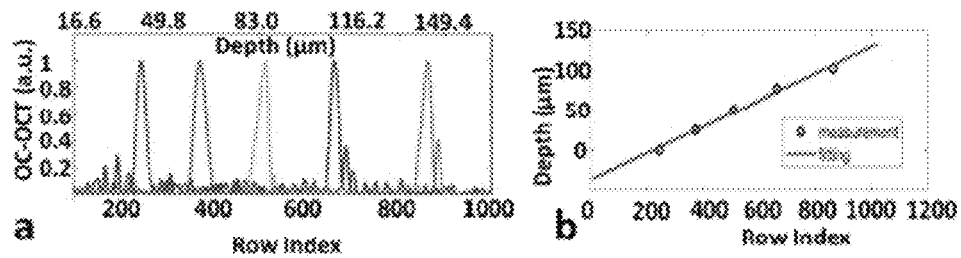
FIGS. 4A-4B show (a) is a graphical depiction of an Ascan obtained from a mirror at different depths; (b) is a graphical depiction of a linear relationship between the nR and the actual depths.

The present inventors first experimentally validated the z sectioning capability of the OC-OCT system. The present inventors assessed the axial point spread function (PSF) of the OC-OCT imaging system, using Ascans obtained from a mirror with an impulse reflectivity profile. The present inventors projected a series of complex exponential functions ($f_n$, n=1, 2, 3, . . . ) to different rows (different y coordinate) of SLM pixels. As a result, different rows of the detector received signals modulated by different complex exponential functions and came from different depths of the sample. The axial PSF (a 1D vector) was then obtained by averaging the image directly obtained from the camera along x direction. The present inventors varied the axial position of the mirror using a translation stage, and obtained axial PSFs as shown in FIG. 4A. The horizontal axis at the bottom of FIG. 4A is the row index (nR) of the sensor array and is linearly related to the depth z: $z=an_R+b$. The present inventors correlated the peak pixel index with the actual axial position of the sample (FIG. 4B) and extracted the values for a and b through linear fitting (a≈0.17 μm and b≈36.91 μm) that allowed the present inventors to convert nR to actual depth shown as the horizontal axis at the top of FIG. 4A. To evaluate the axial resolution, the present inventors used a Gaussian envelop to fit the PSFs obtained at different depths and the axial resolution of the OC-OCT system was estimated to be 5 μm according to the full width half maximum (FWHM) of the Gaussian function. The experimental axial resolution was slightly inferior to the theoretical axial resolution ($\delta z=0.44\lambda_0^2/\Delta\lambda=3.9$ μm given $\lambda_0=470$ nm and $\Delta\lambda=25$ nm), probably because various optical components resulted in a smaller effective spectral bandwidth.

Figures 5A, 5B, 5C, 5D, 5E, 5F:
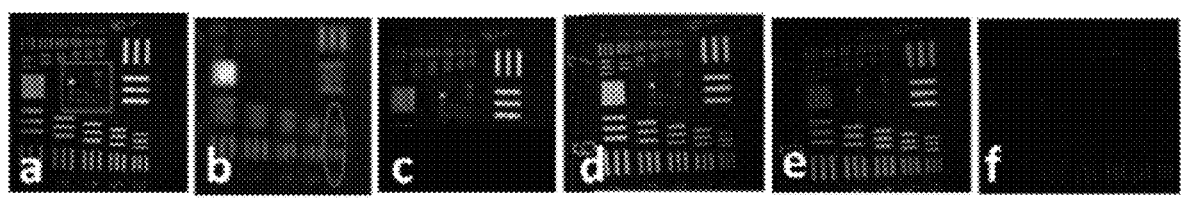
FIGS. 5A-5F show (a) "en face image" of USAF 1951 resolution target; (b) the $6^{th}$ element of the $8^{th}$ group in the resolution target can be resolved; (c) the top part of SLM was programmed to obtain OCT signal from the resolution target; (d)-(f) en face images of the resolution target when the plane chosen by the SLM moved away from the sample surface.

The present inventors demonstrated the capability of the OC-OCT system for depth resolved enface imaging. To achieve enface slicing of the sample at depth $z_0$, the present inventors projected the same modulation pattern ($f_{n0}$) to different rows of the SLM. The present inventors brought the sample, a USAF1951 resolution target, to depth $z_0$ ($z_0=32.30$ m) and obtained the image shown in FIG. 5A. The area within the red square is enlarged in FIG. 5 (b), in which the smallest discernable structure is the $6^{th}$ element of the $8^{th}$ group, suggesting a lateral resolution of 2.2 μm. To validate the image in FIG. 5A was indeed sectioned through optical computation, the present inventors projected $f_{n0}$ to the top rows of the SLM and projected a constant value to pixels at the bottom rows of the SLM. The sample remained at depth $z_0$ and other settings remained unchanged. The resultant OC-OCT image (FIG. 5C) shows large brightness at the top and appears to be completely dark at the bottom. In FIGS. 5D, 5E, and 5F, the present inventors further compared en face images obtained from the resolution target when the SLM modulation pattern selected different imaging depths ($z_0=32.30$ μm, $z_0+1.25$ μm, $z_0+20.5$ μm). When the virtual plane determined by the SLM moved away from sample surface, the brightness of OC-OCT image decreases.

Figures 6A, 6B, 6C, 6D:
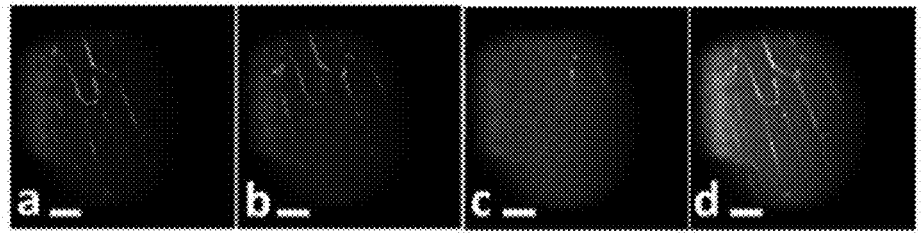
FIGS. 6A-6D show an OC-OCT image of onion skin cells at different depths (a), (b), and (c); (d) image generated by averaging signal at different depths, wherein the scale bars represent 50 μm.

The present inventors also demonstrated OC-OCT for 3D imaging using onion skin cells. The present inventors projected the same Fourier basis function to different rows of the SLM to obtain enface OCT image at a specific depth. By varying the Fourier basis function, the present inventors obtained en face images at different depths in FIGS. 6A, 6B, and 6C with 5 μm axial displacement in between. FIG. 6D is the image obtained by averaging OC-OCT signals within a depth range of 15 μm.

Figures 7A, 7B, 7C, 7D, 7E, 7F, 7G:
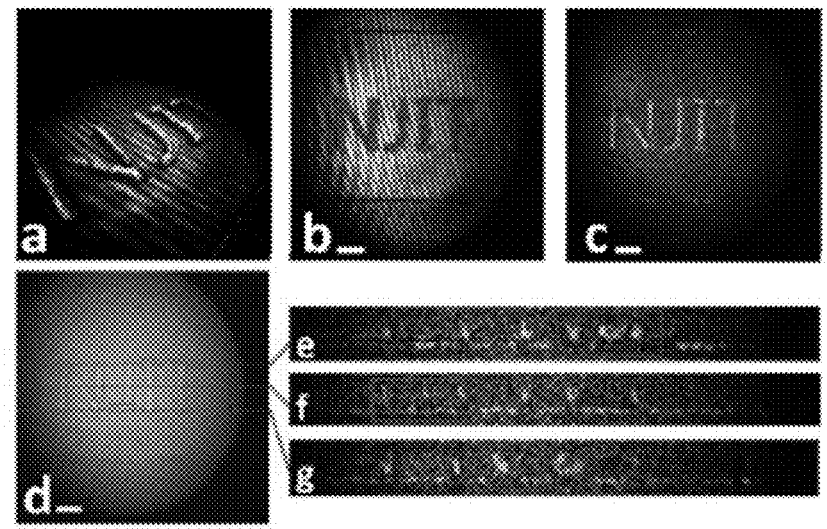
FIGS. 7A-7G show (a) 3D rendering image of 3D phantom: en face image from the substrate (b) and the top of photoresist layer (c); (d) en face image generated by averaging OC-OCT signal within a depth range of 36 μm; (e)-(g) cross sectional images of three positions indicated by red lines in FIG. 7 (d), wherein the scale bars represent 300 μm.

The present inventors also obtained 3D rendered volume through OC-OCT imaging. The present inventors designed lateral patterns on a laser-plotted polyester-based photomask, and fabricated a 3D phantom by depositing photoresist layer (SU-8 2035) with 37 μm elevation on silicon substrate using the photolithography facility at Brookhaven National Laboratory. The present inventors changed the modulation function projected to the SLM to acquire en face OC-OCT data from different depths for volumetric imaging. With 2D images obtained from different depth (29 enface images obtained with a 1.25 μm axial interval), a 3D rendered volume is obtained. FIGS. 7A, 7B and 7C show images corresponding to the surface of silicon substrate and the top of the deposited pattern. FIG. 7D is the image generated by averaging OC-OCT signal at different depths. Along the red lines in FIG. 7D, the present inventors generated cross sectional images (FIGS. 7E, 7F and 7G) using the volumetric data. The rectangles in FIGS. 7E, 7F and 7G correspond to depth profiles for the areas within rectangles of FIG. 7D, from which the top of the letters "I" and "T", middle of the letter "N" and bottom of the letter "J" are discernable.

The OC-OCT system described in the present disclosure enabled optically computed 3D OCT imaging for the first time to the best of the present inventors' knowledge. OC-OCT is fundamentally different from existing technologies that take transverse plane as the preferential scanning dimension. For optical coherence microscopy (OCM) and full field OCT, mechanical scanning cannot be eliminated. One significant advantage of OC-OCT is its flexibility in data acquisition.

In one embodiment of the present disclosure, the present inventors performed 3D imaging by projecting the same Fourier basis function to different rows of the SLM and sequentially acquiring en face images at different depths. If fast imaging is needed in an oblique plane, the OC-OCT system can project different Fourier basis to different rows of the SLM and make the oblique plane the dimension for preferential data acquisition. For structural OCT imaging, the present inventors measured the real and imaginary parts of complex OCT signal with the SLM generating cosine and sine modulations and calculated the amplitude of OCT signal. The real and imaginary parts of complex OCT signal can also be used for phase resolved imaging that is sensitive to nanometer scale displacement, in applications such as optical coherence elastography and imaging cell dynamics. The current OC-OCT system generated temporally interlace cosine and sine patterns for spectral modulation. Hence, its imaging speed was limited by the speed of the SLM (60 Hz refreshing rate). To fully utilize the speed of the camera, complex modulation of interferometric spectrum can also be achieved by projecting spatially interlaced cosine and sine patterns to the SLM.

Optical Computation (OC) for Snap-Shot Phase Resolved OCT Imaging.

Figures 8A, 8B:
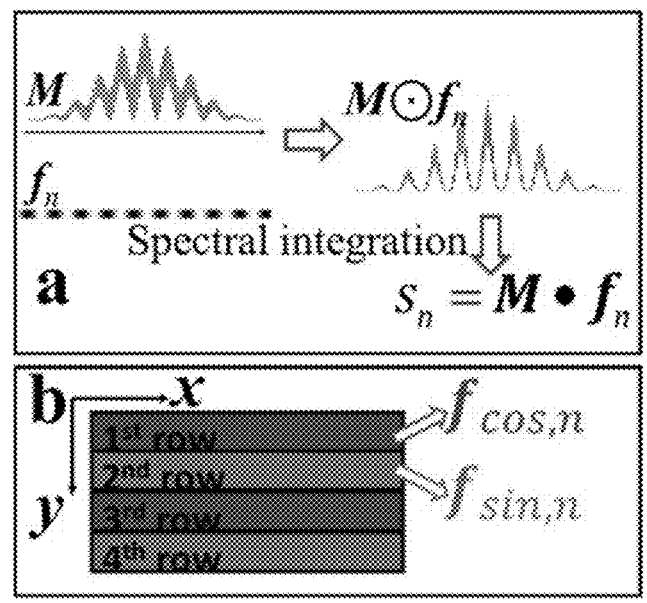
FIGS. 8A-8B show (a) optical computation of Fourier transform by modulating M with $f_n$ projected by the SLM and performing spectrally integration; (b) snap-shot phase imaging by projecting cosine and sin patterns to the SLM.

The inventive OC-OCT allows snap-shot imaging from an oblique plane. In the OCC-OCT system, the reference light and sample light superimpose and go through an optical computation module that directly outputs depth resolved OCT signal. Within the optical computation module, interferometric light is first diffracted by a grating. The spectral interferogram M (M∈ $\mathbb{R}^N$ and M=$[m_1, m_2, m_3, \ldots, m_N]^T$) is then modulated by the spatial light modulator (SLM) (FIG. 8A)). The SLM generates a temporally static modulation pattern, with different transmittance at different pixels. The transmittance is precisely controlled by the value projected to SLM pixels. M is mathematically related to Ascan (complex vector S∈ $\mathbb{C}^N$ and S=$[s_1, s_2, s_3, \ldots, s_N]^T$) at a specific transverse coordinate through Fourier transform: S=FM, where F∈ $\mathbb{C}^{N \times N}$ is the Fourier transform matrix and $F_{nk}=e^{j2\pi nk/N}$. Conventional Fourier domain OCT imaging obtains an Ascan by acquiring the entire spectral interferogram and performing Fourier transform in a computer. For optical computation, we consider the signal at the $n^{th}$ discrete depth in an Ascan ($s_n$) that can be expressed as $s_n=f_n \cdot M$ where · indicates vector inner product and $f_n=[F_{n1}, F_{n2}, F_{n3}, \ldots, F_{nN}]'$. As illustrated in FIG. 8A, the SLM modulates the interferometric spectrum (M) with $f_n$, resulting in elementwise product between these two vectors (M⊙$f_n$).

Modulated by the SLM and diffracted again by a second grating, the light rays originating from the same transverse coordinate at the sample are collimated and detected without spectral discrimination to generate $s_n$ (FIG. 8A). Furthermore, to extract the phase of the complex signal $s_n$ through snap-shot measurement, it is essential to perform Fourier transform using $f_n$ with complex elements. However, the SLM imposes real modulation of light intensity. To address this issue, the SLM generates interlaced cosine ($f_{cos,n}$) and sine ($f_{sin,n}$) functions in its rows along y direction (FIG. 8B), and optically computes the real and imaginary parts of the complex OCT signal.

For structural OCT imaging, the real and imaginary parts of complex OCT signal are measured with the SLM generating cosine and sine modulations and calculated the amplitude of OCT signal. To demonstrate complex OCT imaging, used was the cosine and sine channels output from the OC-OCT system to generate the amplitude and phase of complex signal. The same modulation pattern ($f_{n0}$) was projected to all the rows of the SLM to generate OC-OCT signal from depth $z_0$. Used then was the OC-OCT system to image the substrate and the top of the 3D phantom fabricated by photolithography. In summary, the OC-OCT system described enabled optically computed complex OCT imaging for the first time to the best of the inventor's knowledge.

The present inventors designed the magnification from the sample plane to the SLM plane, such that the diffraction limited spot size at the sample is mapped to more than two SLM pixels. As a result, the binning of SLM pixels in y dimension to extract complex OCT signal will not lead to reduced axial resolution.

By taking snapshot measurement of g∈ $\mathbb{R}^{Nx \times Ny}$, the magnitude (Eq (3))

$$I_{i,j}=\sqrt{g_{i,2j}^2+g_{i,2j-1}^2} \quad (3)$$

wherein $I_{i,j}$ is the magnitude of complex OCT signal and is proportional to the optical field reflected or scattered from the sample, and $g_{i,2j}$ and $g_{i,2j-1}$ are snapshot measurements taken at different rows of the camera, modulated by the SLM with sinusoidal signals with a 90 degree phase difference; and phase (Eq (4)) of the complex OCT signal, $$\phi_{i,j} = \mathrm{atan}\left(\frac{g_{i,2j}}{g_{i,2j-1}}\right) \quad (4)$$

wherein $\phi_{i,j}$ is the phase of the complex OCT signal and $g_{i,2j}$ and $g_{i,2j-1}$ are snapshot measurements taken at different rows of the camera, modulated by the SLM with sinusoidal signals with a 90 degree phase difference;

as well as the sub-nanometer displacement used for dynamic imaging (Eq (5)), can be extracted, $$d_{i,j} = \frac{\lambda}{4n\pi}\mathrm{atan}\left(\frac{g_{i,2j}}{g_{i,2j-1}}\right) \quad (5)$$

wherein $d_{i,j}$ is the subnanometer displacement, $\lambda_0$ is an initial signal, n is the refractive index, and $g_{i,2j}$ and $g_{i,2j-1}$ are snapshot measurements taken at different rows of the camera, modulated by the SLM with sinusoidal signals with a 90 degree phase difference.

Notably, for pixels at different transverse coordinates, the signal formation mechanism remains the same as described above, because the optical computation module establishes a one-to-one mapping between transverse coordinates (x and y) at the sample plane and those at the detector plane (illustrated as solid and dashed light beam profiles in FIG. 8A). Hence the 2D output of the optical computation module is OCT signal from an en face plane at the $n^{th}$ descrite depth of $f_n$ is projected by the SLM. A different axial position can be selected by projecting a different Fourier basis function.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

REFERENCES

1. D. Huang, E. A. Swanson, C. P. Lin, J. S. Schuman, W. G. Stinson, W. Chang, M. R. Hee, T. Flotte, K. Gregory, and C. A. Puliafito, "Optical coherence tomography," science 254, 1178-1181 (1991).
2. Y. Jia, S. T. Bailey, D. J. Wilson, O. Tan, M. L. Klein, C. J. Flaxel, B. Potsaid, J. J. Liu, C. D. Lu, and M. F. Kraus, "Quantitative optical coherence tomography angiography of choroidal neovascularization in age-related macular degeneration," Ophthalmology 121, 1435-1444 (2014).
3. Y. Qiu, Y. Wang, Y. Xu, N. Chandra, J. Haorah, B. Hubbi, B. J. Pfister, and X. Liu, "Quantitative optical coherence elastography based on fiber-optic probe for in situ measurement of tissue mechanical properties," Biomedical Optics Express 7, 688-700 (2016).

4. T. Akkin, D. Landowne, and A. Sivaprakasam, "Detection of neural action potentials using optical coherence tomography: intensity and phase measurements with and without dyes," Frontiers in neuroenergetics 2, 22 (2010).
5. M. Wojtkowski, V. Srinivasan, J. G. Fujimoto, T. Ko, J. S. Schuman, A. Kowalczyk, and J. S. Duker, "Three-dimensional retinal imaging with high-speed ultrahigh-resolution optical coherence tomography," Ophthalmology 112, 1734-1746 (2005).
6. R. Leitgeb, C. K. Hitzenberger, and A. F. Fercher, "Performance of fourier domain vs. time domain optical coherence tomography," Opt. Express 11, 889-894 (2003).
7. M. A. Choma, M. V. Sarunic, C. Yang, and J. A. Izatt, "Sensitivity advantage of swept source and Fourier domain optical coherence tomography," Opt. Express 11, 2183-2189 (2003).
8. D. R. Solli and B. Jalali, "Analog optical computing," Nature Photonics 9, 704 (2015).
9. W. Zhang, X. Zhang, C. Wang, W. Liao, S. Ai, J. Hsieh, N. Zhang, and P. Xue, "Optical computing optical coherence tomography with conjugate suppression by dispersion," Opt. Lett. 44, 2077-2080 (2019).
10. C. Maurer, A. Jesacher, S. Bernet, M. Ritsch-Marte, Laser & Photonics Reviews. 5(1):81-101 (2011).
11. Z. Zhang, X. Ma, and J. Zhong, "Single-pixel imaging by means of Fourier spectrum acquisition," Nature Communications 6, 6225 (2015).
12. X. Liu, M. Balicki, R. H. Taylor, and J. U. Kang, "Towards automatic calibration of Fourier-Domain OCT for robot-assisted vitreoretinal surgery," Opt. Express 18, 24331-24343 (2010).

What is claimed is:

1. A method for optically computed optical coherence tomography (OC-OCT), comprising:
    performing depth-resolved imaging in 3D space by using an optically computer optical coherence tomography (OC-OCT) to observe a structure and a dynamics of an object noninvasively inside a patient or a sample;
    allowing an optical computation of a Fourier transform of an interferometric spectra to reconstruct the depth resolved image before image data acquisition;
    using a spatial light modulator (SLM) to manipulate a light wave to generate output with a desired amplitude and phase for computation and to produce a scan-less three dimensional (3D) OCT image;
    wherein the optical computation of the Fourier transform further includes modulating the interferometric spectra with the SLM that is programmable, and spectrally non-discriminative detection of the object by integrating optical energy from all wavelengths of the interferometric spectra modulated by the SLM for visualizing neural activity and blood flow dynamics of the object inside the patient or the sample;
    allowing modification of the SLM for a cosine pattern and a sine pattern to be projected to the SLM;
    temporally interlacing the cosine pattern and the sine pattern for spectral modulation;
    synchronizing data acquisition with alternation of the cosine pattern and the sine pattern, acquiring signals from cosine and sine channels and extracting a magnitude of OC-OCT signal; and
    wherein the OC-OCT system eliminates mechanical scanning in tomographic imaging and performs computation optically of the image without requiring transfer of image data into a computer to perform computation tasks for image reconstruction and data analysis; and
    performing fast imaging in a snap-shot manner in the en face plane that is orthogonal to the direction of light propagation or in an oblique plane of the patient or the sample.

2. The method of claim 1, further comprising modulating the interferometric spectra with Fourier basis function projected to a spatial light modulator (SLM) and detecting the modulated signal without spectral discrimination.

3. The method of claim 1, wherein the OC-OCT system manipulates optical signals in both spatial and spectral domain for computation.

4. The method of claim 1, wherein the imaging is done on a biological tissue.

5. The method of claim 4, wherein the biological tissue is soft tissue, and wherein the soft tissue is deep tissue selected from the group consisting of breast tissue, skin, brain tissue, muscles, tendons, ligaments, connective tissue, lung tissue, liver tissue, kidney tissue, intestinal tissue, stomach tissue, heart tissue, bladder tissue, pancreatic tissue, spleen tissue, and any combination thereof.

6. The method of claim 1 further includes obtaining in situ 3D imaging of the biological tissue.

7. The method of claim 1 further includes extracting a signal from a specific depth in the object directly without signal processing in a computer; and wherein depth resolution is achieved by optically Fourier transforming a spectral interferogram.

8. The method of claim 1 further includes phase resolved volumetric OCT imaging without mechanical scanning, and imaging an arbitrary 2D plane in a snapshot manner.

* * * * *